· US008910376B2

(12) United States Patent
McDonald

(10) Patent No.: US 8,910,376 B2
(45) Date of Patent: Dec. 16, 2014

(54) SYSTEMS AND METHODS FOR FORMING AN END OF AN ELONGATED MEMBER OF AN ELECTRICAL STIMULATION SYSTEM

(75) Inventor: Matthew Lee McDonald, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1048 days.

(21) Appl. No.: 12/473,170

(22) Filed: May 27, 2009

(65) Prior Publication Data

US 2010/0304626 A1   Dec. 2, 2010

(51) Int. Cl.
*H01R 43/00* (2006.01)
*H01R 24/58* (2011.01)
*H01R 24/76* (2011.01)
*H01R 4/18* (2006.01)
*H01R 4/20* (2006.01)
*A61N 1/05* (2006.01)
*H01R 13/33* (2006.01)
*H01R 107/00* (2006.01)

(52) U.S. Cl.
CPC .............. *H01R 24/58* (2013.01); *A61N 1/0551* (2013.01); *H01R 24/76* (2013.01); *H01R 4/183* (2013.01); *H01R 13/33* (2013.01); *H01R 4/20* (2013.01); *H01R 2107/00* (2013.01)
USPC ................... 29/857; 29/852; 29/850; 29/845; 29/842; 607/115; 607/116; 607/119; 607/122; 604/20

(58) Field of Classification Search
CPC ........ A61N 1/0551; H01R 4/20; H01R 4/183; H01R 24/58; H01R 24/76
USPC ........... 29/832, 830, 831, 852, 850, 845, 842, 29/857; 439/668, 363, 397, 401, 402, 658; 604/20; 607/115, 116, 119, 122–128
See application file for complete search history.

(56) References Cited

U.S. PATENT DOCUMENTS

| | | |
|---|---|---|
| 3,788,329 A | 1/1974 | Friedman |
| 4,945,922 A | 8/1990 | van Krieken et al. |
| 4,954,105 A | 9/1990 | Fischer |
| 5,275,171 A | 1/1994 | Barcel |
| 5,431,681 A | 7/1995 | Helland |

(Continued)

OTHER PUBLICATIONS

U.S. Appl. No. 11/238,240, filed Sep. 29, 2005 (20 pgs.).

*Primary Examiner* — Peter DungBa Vo
*Assistant Examiner* — Jeffrey T Carley
(74) *Attorney, Agent, or Firm* — Lowe Graham Jones; Bruce E. Black

(57) ABSTRACT

A method for forming a lead or lead extension having an arrangement of elongated conductors disposed in a body of a lead or lead extension includes ablating a plurality of spaced-apart channels in proximity to at least one of the proximal end or the distal end of the body to expose at least part of at least one of the conductors. A C-shaped contact is disposed into each of a different one of the transverse channels. Each C-shaped contact is electrically coupled to at least one of the conductors. Each C-shaped contact is closed so that opposing ends of the C-shaped contact are adjacent to one another and aligned over one of the elongated conductors. The two opposing ends of each C-shaped contact is coupled together such that each C-shaped contact forms a continuous path around the arrangement within the transverse channel in which the C-shaped contact is disposed.

18 Claims, 7 Drawing Sheets

(56) References Cited

U.S. PATENT DOCUMENTS

| | | | |
|---|---|---|---|
| 5,458,629 A * | | 10/1995 | Baudino et al. ............... 607/116 |
| 5,466,254 A | | 11/1995 | Helland |
| 5,674,274 A | | 10/1997 | Morgan et al. |
| 5,796,044 A | | 8/1998 | Cobian et al. |
| 5,928,277 A | | 7/1999 | Laske et al. |
| 5,935,159 A | | 8/1999 | Cross, Jr. et al. |
| 5,967,977 A | | 10/1999 | Mullis et al. |
| 6,018,684 A | | 1/2000 | Bartig et al. |
| 6,171,275 B1 * | | 1/2001 | Webster, Jr. .................... 604/20 |
| 6,181,969 B1 | | 1/2001 | Gord |
| 6,185,463 B1 * | | 2/2001 | Baudino ....................... 607/119 |
| 6,249,708 B1 | | 6/2001 | Nelson et al. |
| 6,253,111 B1 | | 6/2001 | Carner |
| 6,278,897 B1 | | 8/2001 | Rutten et al. |
| 6,295,476 B1 | | 9/2001 | Schaenzer |
| 6,324,415 B1 | | 11/2001 | Spehr et al. |
| 6,361,531 B1 * | | 3/2002 | Hissong ........................ 606/27 |
| 6,377,857 B1 | | 4/2002 | Brayton et al. |
| 6,400,992 B1 | | 6/2002 | Borgersen et al. |
| 6,477,396 B1 * | | 11/2002 | Mest et al. .................... 600/374 |
| 6,477,427 B1 | | 11/2002 | Stolz et al. |
| 6,516,227 B1 | | 2/2003 | Meadows et al. |
| 6,516,232 B2 | | 2/2003 | Skinner |
| 6,609,029 B1 | | 8/2003 | Mann et al. |
| 6,609,032 B1 | | 8/2003 | Woods et al. |
| 6,662,055 B1 | | 12/2003 | Prutchi |
| 6,701,191 B2 | | 3/2004 | Schell |
| 6,741,892 B1 | | 5/2004 | Meadows et al. |
| 6,973,351 B2 | | 12/2005 | Morgan |
| 7,244,150 B1 | | 7/2007 | Brase et al. |
| 7,555,349 B2 | | 6/2009 | Wessman et al. |
| 2002/0042643 A1 | | 4/2002 | Skinner |
| 2003/0114905 A1 | | 6/2003 | Kuzma |
| 2003/0199959 A1 | | 10/2003 | Zhang et al. |
| 2004/0059392 A1 | | 3/2004 | Parramon et al. |
| 2005/0165465 A1 | | 7/2005 | Pianca et al. |
| 2006/0111768 A1 | | 5/2006 | Wessman et al. |
| 2006/0122682 A1 | | 6/2006 | Sommer et al. |
| 2006/0247749 A1 | | 11/2006 | Colvin |
| 2006/0252314 A1 | | 11/2006 | Atalar et al. |
| 2006/0259106 A1 | | 11/2006 | Arnholt et al. |
| 2007/0038278 A1 | | 2/2007 | Zarembo |
| 2007/0038280 A1 | | 2/2007 | Bodner et al. |
| 2007/0142890 A1 | | 6/2007 | Zarembo et al. |
| 2007/0150007 A1 | | 6/2007 | Anderson et al. |
| 2007/0150036 A1 | | 6/2007 | Anderson |
| 2007/0161294 A1 | | 7/2007 | Brase et al. |
| 2007/0184197 A1 | | 8/2007 | Aron et al. |
| 2007/0219595 A1 | | 9/2007 | He |
| 2007/0239243 A1 | | 10/2007 | Moffitt et al. |
| 2007/0239249 A1 | | 10/2007 | Tockman et al. |
| 2008/0071320 A1 | | 3/2008 | Brase |

* cited by examiner

SYSTEMS AND METHODS FOR FORMING AN END OF AN ELONGATED MEMBER OF AN ELECTRICAL STIMULATION SYSTEM

FIELD

The present invention is directed to the area of implantable electrical stimulation systems and methods of making and using the systems. The present invention is also directed to systems and methods of forming one or more ends of elongated members of electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a method for forming a lead or lead extension having an arrangement of a plurality of elongated conductors disposed in a body of the lead or lead extension, each of the elongated conductors extending from a proximal end of the arrangement to a distal end of the arrangement, includes ablating a plurality of spaced-apart channels in proximity to at least one of the proximal end or the distal end of the body to expose at least part of at least one of the plurality of elongated conductors. A C-shaped contact is disposed into each of a different one of the transverse channels. Each of the C-shaped contacts is electrically coupled to at least one of the elongated conductors. Each of the C-shaped contacts is closed so that opposing ends of the C-shaped contact are adjacent to one another and aligned over one of the elongated conductors. For each of the C-shaped contacts, the two opposing ends are coupled together such that the C-shaped contact forms a continuous path around the arrangement within the transverse channel in which the C-shaped contact is disposed.

In another embodiment, a method for forming a lead or lead having an arrangement of a plurality of elongated conductors disposed in a body of the lead or lead extension, each of the elongated conductors extending from a proximal end of the arrangement to a distal end of the arrangement, includes ablating a plurality of access ports in at least one of the proximal end or the distal end of the body, each of the access ports exposing one of the elongated conductors. C-shaped contacts are disposed over each of the access ports such that each C-shaped contact is disposed over at least one of the access ports. The C-shaped contacts are electrically coupled to at least one of the elongated conductors. Each of the C-shaped contacts is closed so that the two opposing ends of the C-shaped contacts are adjacent to one another. For each of the C-shaped contacts, the two opposing ends are coupled together such that the C-shaped contact forms a continuous path around the arrangement over the at least one access port over which the C-shaped contact is disposed.

In yet another embodiment, a lead includes a lead body with an outer layer and having a distal end, a proximal end, and a transverse circumference. The lead body defines a plurality of spaced-apart channels around the transverse circumference of the lead body in proximity to at least one of the distal end or the proximal end of the lead body. The lead body includes a plurality of cylindrical electrodes disposed on the distal end of the lead body, a plurality of cylindrical terminals disposed on the proximal end of the lead body, and a plurality of conductors, each conductor electrically coupling at least one of the electrodes to at least one of the terminals. At least one of the plurality of electrodes or at least one of the plurality of terminals includes a C-shaped contact that has been disposed over the transverse circumference of the lead body and closed with opposing ends of the C-shaped contact coupled together. The opposing ends of the C-shaped contact define a coupling aperture. At least one of the plurality of conductors extends into the coupling aperture and electrically couples to the C-shaped contact.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to systems and methods of forming one or more ends of elongated members of electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent applications Ser. Nos. 10/353,101, 10/503,281, 11/238,240; 11/319,291; 11/327,880; 11/375,638; 11/393,991; and 11/396,309, all of which are incorporated by reference.

Figure 1:
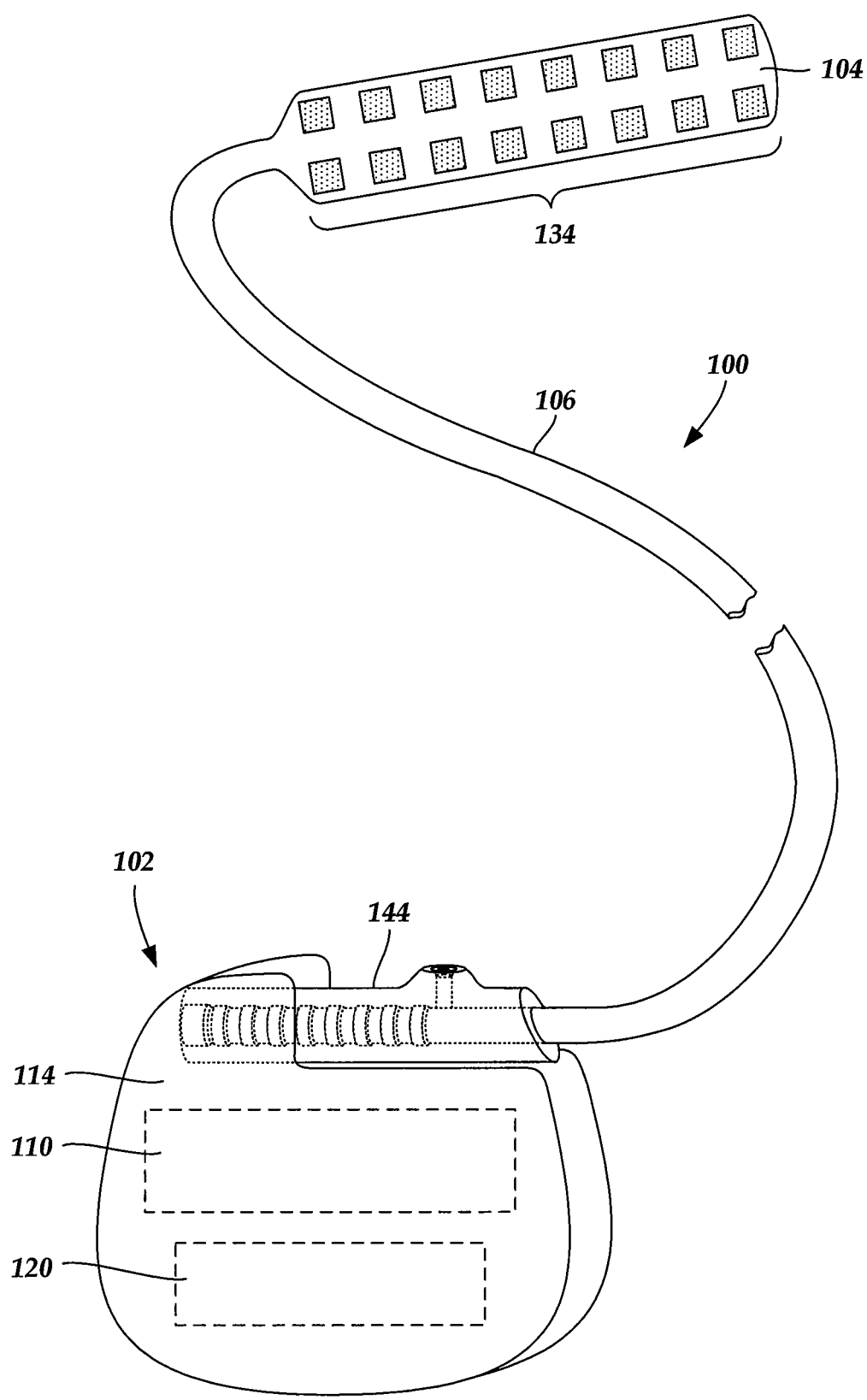
FIG. 1 is a schematic view of one embodiment of an electrical stimulation system, according to the invention.
Figure 2:
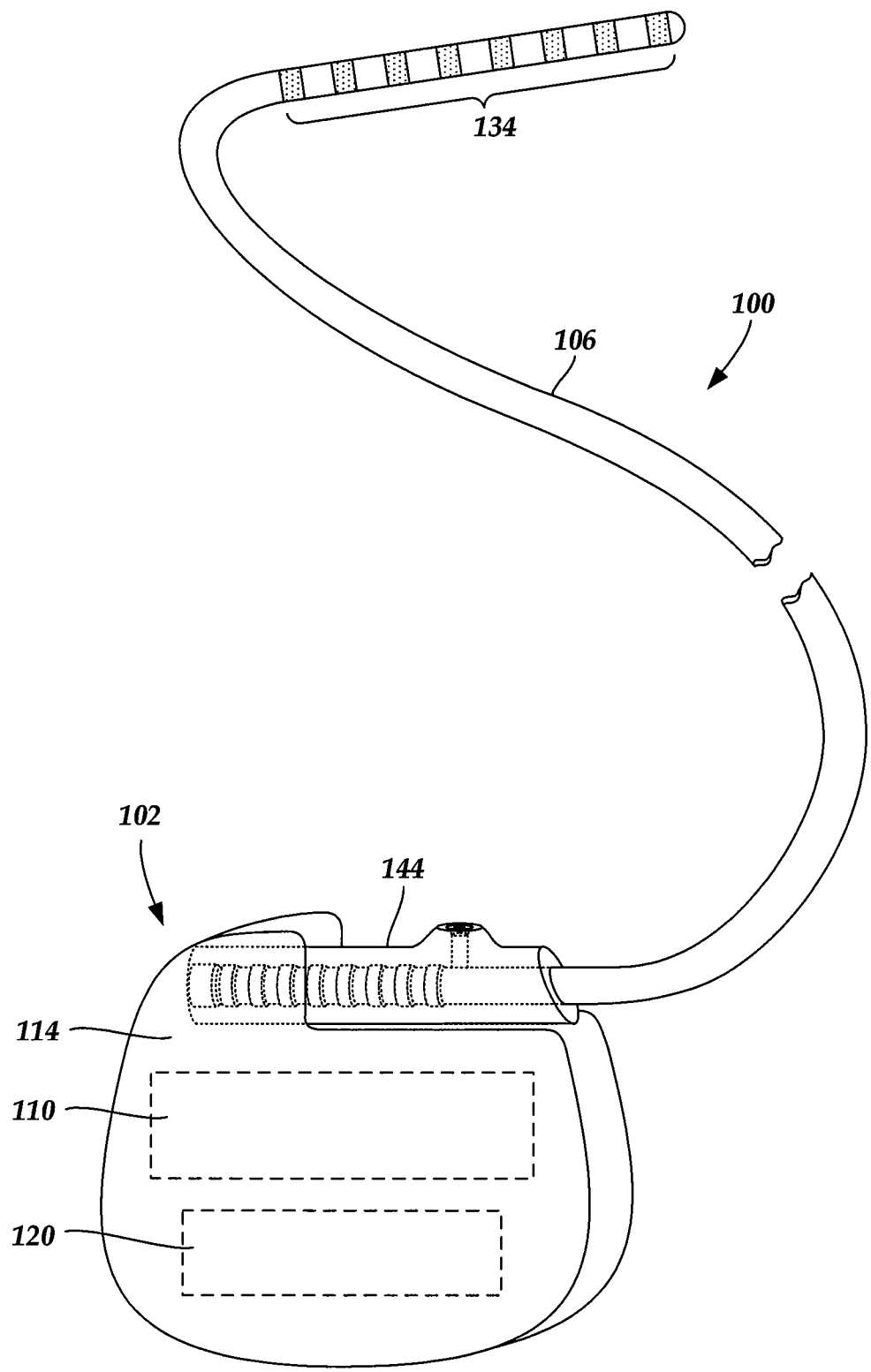
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via connector contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding connector contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as connector contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
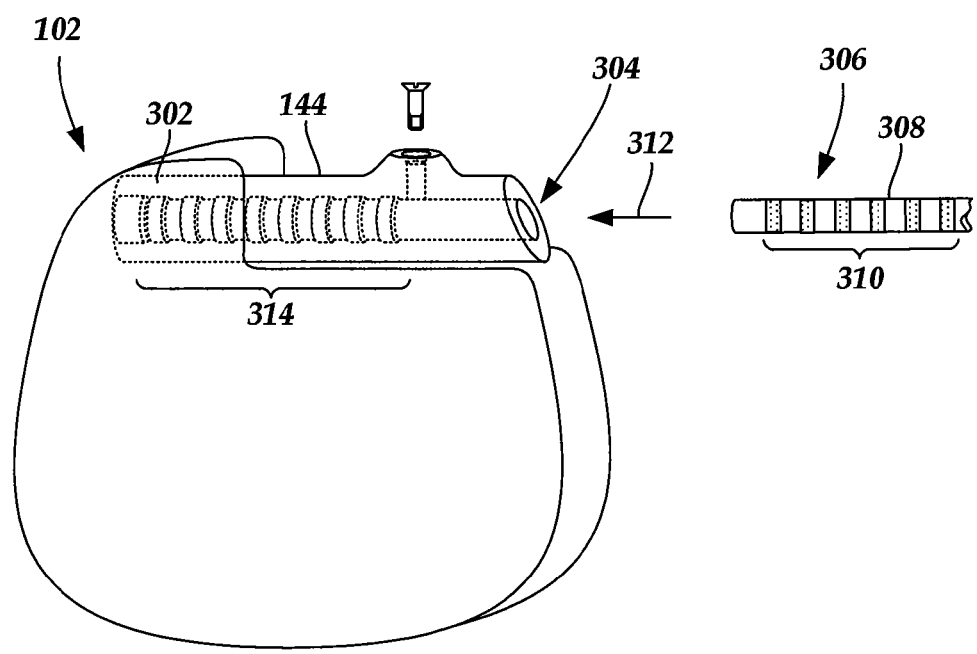
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of connector contacts 314 for each port 304. When the lead 308 is inserted into the port 304, the connector contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat.

No. 7,244,150 and U.S. patent application Ser. No. 11/532,844, which are incorporated by reference.

Figure 3B:
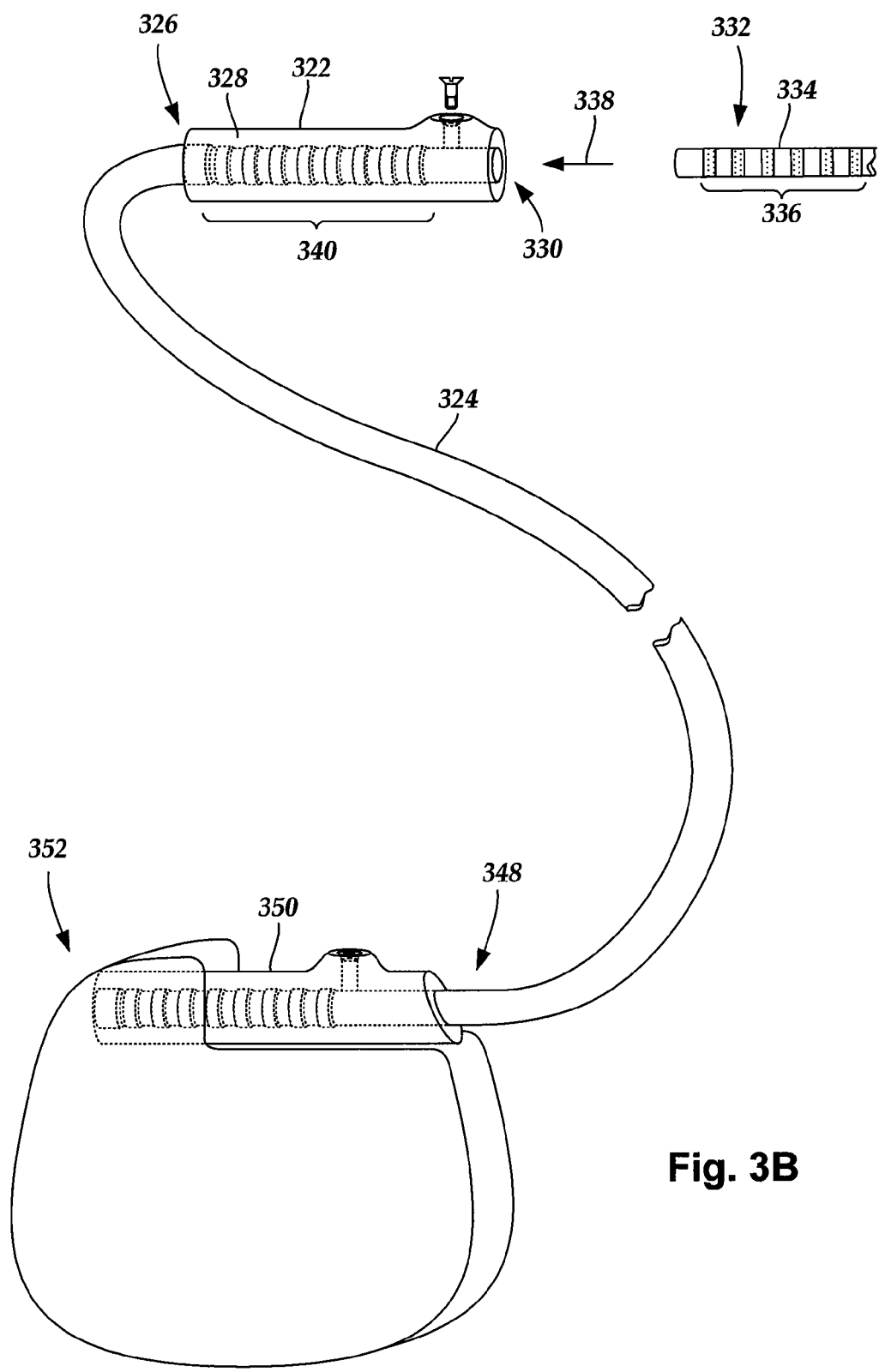
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of connector contacts 340. When the lead 334 is inserted into the port 330, the connector contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) disposed in a body of the lead extension that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

Assembling the ends of an elongated member (e.g., a lead, a lead extension, or the like) may be complex, tedious, and expensive. For example, with conventional methods, the proximal end of the body of the elongated member is typically radially ablated to expose underlying conductors extending within the body of the elongated member. Cylindrical contacts (e.g., terminals) are placed over the exposed conductors in a spaced-apart manner with one or more non-conductive spacers positioned between adjacent contacts. Each of the contacts is electrically coupled to a different one of the conductors. Additional steps may also be necessary including, for example, back filling lumens in which the conductors are disposed with epoxy and grinding the contacts to size so that outer surfaces of the contacts are flush with outer surfaces of the elongated body. In some cases (e.g., with percutaneous leads), the distal end of the elongated members may be assembled in a similar manner, with the contacts being electrodes instead of terminals. In other cases (e.g., with lead extensions), the distal end of the elongated members may be assembled in a similar manner, with the contacts being connector contacts instead of terminals.

In at least some embodiments, a plurality of spaced-apart C-shaped contacts may be disposed over portions of the elongated member and electrically coupled to underlying conductors extending within the elongated member. In at least some embodiments, each of the C-shaped contacts has opposing inwardly-bending ends that wrap around a transverse axis of the elongated member and that may be closed and coupled together to form a continuous path around the transverse axis of the elongated member. In at least some embodiments, portions of the elongated member may be ablated to form spaced-apart transverse channels that are configured and arranged to receive C-shaped contacts and that provide access to electrically couple the C-shaped contacts to the underlying conductors.

Typically, the elongated member includes an arrangement of elongated conductors disposed in an outer layer. The conductors may be disposed in elongated members in many different possible configurations (e.g., arranged into units, coiled into a helical configuration, disposed in a multi-lumen retention element, disposed over a sleeve, disposed over a mandrel, or the like). Additionally, in at least some embodiments, the conductors are also individually encased by a layer of insulation. It will be understood that, when the conductors are individually encased by a layer of insulation, the layer of insulation encasing the conductor may also be ablated to expose underlying conductors.

Figure 4:
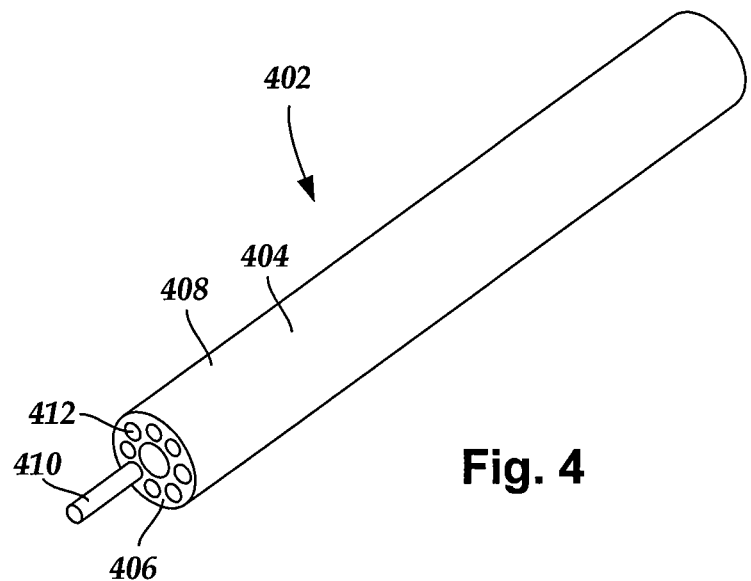
FIG. 4 is a schematic perspective view of one embodiment of a proximal end of an elongated member, according to the invention.

In at least some embodiments, the conductors are disposed in a multi-lumen retention element. FIG. 4 is a schematic perspective view of one embodiment of an elongated member 402. The elongated member 402 includes a body 404. The body 404 includes a multi-lumen retention element 406 and an outer layer 408. In at least some embodiments, the outer layer 408 is part of the multi-lumen retention element 406. One or more conductors, such as conductor 410, may be disposed in one or more of the lumens, such as lumen 412. It will be understood that the conductor 410 is shown extending from the elongated member 402 for clarity of illustration.

To electrically couple the conductors to contacts, the conductors are exposed. One technique for exposing the conductors is ablating portions of the outer layer 408 of the elongated member 402. In at least some embodiments, the outer layer 408 of the elongated member 402 is ablated to form spaced-apart transverse channels to access a plurality of the conductors and also to receive a C-shaped contact. In preferred embodiments, the transverse channels are laser ablated.

Figure 5:
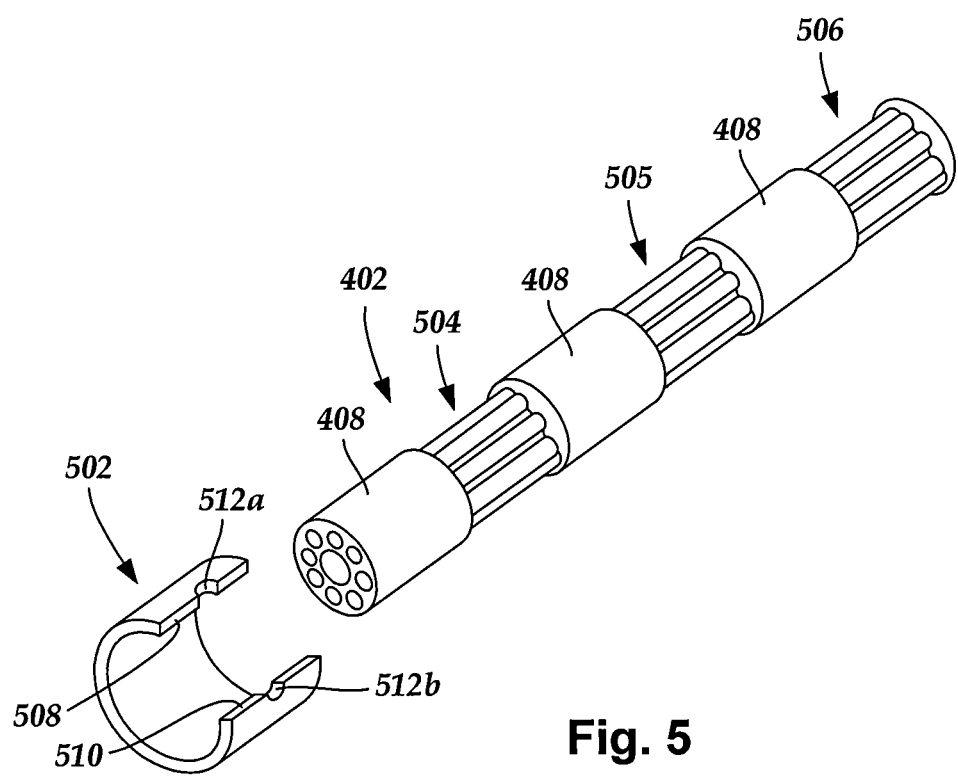
FIG. 5 is a schematic perspective view of one embodiment of a proximal end of an elongated member and a C-shaped contact, the elongated member having transverse channels ablated into the elongated member to expose conductors extending within the elongated member, according to the invention.

FIG. 5 is a schematic perspective view of one embodiment of the elongated member 402 and a C-shaped contact 502. The outer layer 408 of the elongated member 402 has been ablated to form transverse channels 504-506 extending along a transverse axis of the elongated member. The transverse channels 504-506 are deep enough to expose a plurality of underlying conductors when conductors are disposed in the elongated member 402. It will be understood that, when conductors are disposed in the lumens of the multi-lumen retention element 406, an outer portion of the multi-lumen retention element 406 may also be ablated to expose the conductors. In some embodiments, the outer portion of the multi-lumen retention element 404 is ablated before the conductors are disposed in the multi-lumen retention element 404. In other embodiments, the outer portion of the multi-lumen retention element 404 is ablated after the conductors are disposed in the multi-lumen retention element 406.

The C-shaped contact 502 includes two opposing inwardly-bending ends 508 and 510. In at least some embodiments, each of the opposing ends define a portion of a coupling aperture 512a and 512b, respectively, which collectively form a coupling aperture (512 in FIG. 7) when the C-shaped contact 502 is closed, as described below.

The C-shaped contact 502 may be formed from any biocompatible conductive material suitable for implantation into a patient including, for example, metals (e.g., platinum, iridium, and the like), alloys, conductive polymers, conductive carbon, and the like, as well as combinations thereof.

Figure 6:
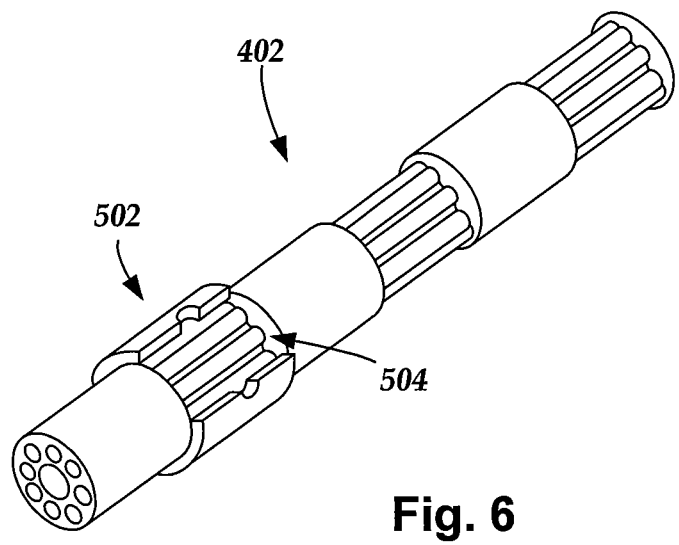
FIG. 6 is a schematic perspective view of one embodiment of the C-shaped contact of FIG. 5 disposed over a transverse channel ablated into the elongated member of FIG. 5, according to the invention.
Figure 7:
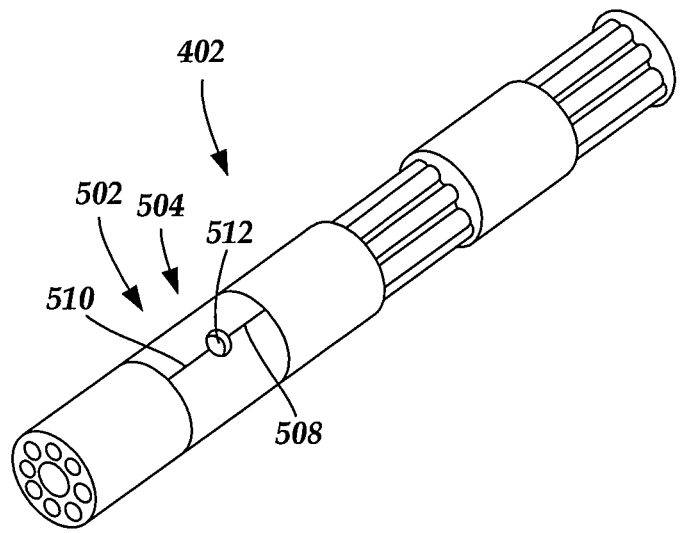
FIG. 7 is a schematic perspective view of one embodiment of the C-shaped contact of FIG. 5 disposed over a transverse channel ablated into the elongated member of FIG. 5 with opposing inwardly-bending ends of the C-shaped contact coupled together to form a continuous path around the transverse channel, according to the invention.

In at least some embodiments, the C-shaped contact 502 defines a transverse length between the opposing inwardly-bending ends 508 and 510. In some embodiments, the transverse length of the C-shaped contact 502 is equal to a transverse circumference of the ablated portion of the transverse channels 504-506 of the elongated body 402. In other embodiments, the transverse length of the C-shaped contact 502 is equal to a transverse circumference of the outer layer 408 of the elongated body 402. In some embodiments, the C-shaped contact 502 is configured and arranged to be disposed in the transverse channels 504-506 (as described below and as shown in FIGS. 6 and 7). In other embodiments, the C-shaped contact 502 is configured and arranged to be disposed over the outer layer 408 of the elongated member 402.

It may be an advantage for an elongated member to be isodiametric. An isodiametric elongated member may reduce the chance of the elongated member getting caught on patient tissue during insertion of the elongated member into the patient, or during patient movement subsequent to implantation of the elongated member.

It may be an advantage to inset the C-shaped contact 502 in the transverse channel 504 because the C-shaped contact 502 may be formed with a transverse cross-sectional profile that is thicker than with conventional contacts, when the elongated member is isodiametric. A thicker contact may promote better electrical contact and may increase durability of the electrical stimulation system. It may further be an advantage to inset the C-shaped contact 502 in the transverse channel 504 because the thickness of the transverse cross-sectional profile of the C-shaped contact 502 may be formed so that an outer surface of the C-shaped contact 502 is flush with the outer layer 408 of the elongated member without needing to grind down the C-shaped contact 502. In other embodiments, there can be grinding of the lead (e.g., the contacts, the lead body, or both) to form an isodiametric lead.

FIG. 6 is a schematic perspective view of one embodiment of the C-shaped contact 502 disposed in the transverse channel 504 of the elongated member 402. In at least some embodiments, the C-shaped contact 502 is flexible. In at least some embodiments, the C-shaped contact 502 is disposed within the transverse channel 504. For example, in at least some embodiments the C-shaped contact 502 is snapped over the transverse channel 504. In at least some embodiments, the depth of the transverse channel 504 is no greater than the thickness of the C-shaped contact 502. In at least some embodiments, the depth of the transverse channel 504 is equal to the thickness of the C-shaped contact 502.

Accordingly, in at least some embodiments, when the C-shaped contacts are disposed in the transverse channels, an outer surface of the C-shaped contact 502 is flush with outer surfaces of the elongated member 402. Alternatively, in at least some other embodiments, the outer surfaces of the C-shaped contact 502 extend radially outward from the outer surfaces of the elongated member 402. In which case, the outer surfaces of the C-shaped contact 502 may be ground down to be flush with the outer surfaces of the elongated member 402.

In at least some embodiments, once the C-shaped contact 502 is disposed over one of the transverse channels, the C-shaped contact 502 is closed (e.g., crimped, clamped, squeezed, or the like) so that the opposing inwardly-bending ends 508 and 510 of the C-shaped contact 502 are adjacent to one another. FIG. 7 is a schematic perspective view of one embodiment of the C-shaped contact 502 disposed over the transverse channel 504 of the elongated member 402. The opposing ends 508 and 510 of the C-shaped contact 502 are closed so that the opposing inwardly-bending ends 508 and 510 are adjacent to one another. In at least some embodiments, a tooling fixture may be used to close the C-shaped contact 502. In at least some embodiments, when the opposing ends 508 and 510 are closed, the portions of the coupling aperture (512a and 512b of FIG. 5) align to form a complete coupling aperture 512.

Once the C-shaped contact 502 is closed, the opposing ends 508 and 510 of the C-shaped contact 502 may be coupled together to form a continuous path around a transverse circumference of the elongated member 402. In preferred embodiments, the opposing ends 508 and 510 are coupled together using an electrically-conductive medium (e.g., welding, soldering, or the like).

In at least some embodiments, the closed opposing ends 508 and 510 of the C-shaped contact 502 may be aligned around the transverse circumference of the elongated member 402 such that the coupling aperture 512 aligns with one of the conductors. In at least some embodiments, when the coupling aperture 512 is aligned with one of the conductors, electrically coupling the opposing ends 508 and 510 of the C-shaped contact 502 together also electrically couples the aligned conductor to the C-shaped contact 502, via the coupling aperture 512. For example, the aligned conductor may be extended through the coupling aperture 512 so that coupling the opposing ends 508 and 510 of the C-shaped contact 502 also couples the conductor to the C-shaped contact 502. It will be understood that, when multiple C-shaped contacts are coupled to the elongated member 402, each of the coupling apertures of different C-shaped contacts may be aligned with different conductors.

In alternate embodiments, one of the underlying conductors may be electrically coupled to the C-shaped contact 502 prior to the C-shaped contacts being closed. For example, the C-shaped contact 502 may be disposed within the transverse channel 504 in an open position and one of the underlying conductors accessible from one of the transverse channels 504 may be coupled to an undersurface of the C-shaped contact 502, or coupled to one of the opposing ends (preferably within a portion of one of the coupling apertures) of the C-shaped contact 502. The C-shaped contact 502 may subsequently be closed and the ends of the C-shaped contact 502 may be coupled together. In at least some embodiments, coupling the C-shaped contact 502 is performed by an automated system. It may be an advantage to employ an automated system to increase one or more of productivity or consistency.

In at least some other embodiments, one or more access holes may by ablated in the elongated body in addition to, or in lieu of, ablating one or more transverse channels. One or more access holes may be ablated through the outer layer 408 to access one of the conductors individually, without accessing multiple conductors. It may be an advantage to ablate individual access holes instead of ablating transverse channels to prevent undesired conductors from contacting the C-shaped contact and potentially causing a short circuit.

When one or more access holes are ablated in the elongated body, the C-shaped contact 502 may be disposed over the outer layer 408 of the elongated body and the C-shaped contact 502 may be electrically coupled to the underlying conductor via the one or more access holes. In some embodiments, the C-shaped contact 502 is electrically coupled to the underlying conductor prior to coupling the C-shaped contact 502, in a similar manner as describe above. In other embodiments, the C-shaped contact 502 is closed without being electrically coupled to the conductors. Then, once the C-shaped contact 502 is closed, the coupling aperture 512 of the C-shaped contact 502 is aligned over at least one of the access holes and the C-shaped contact 502 is electrically coupled to the underlying conductor, via the coupling aperture 512, as the opposing ends 508 and 510 of the C-shaped contact 502 are coupled together. In at least some embodiments, the underlying conductor is extended through the coupling aperture 512 when the opposing ends 508 and 510 of the C-shaped contact 502 are coupled together.

Figure 8:
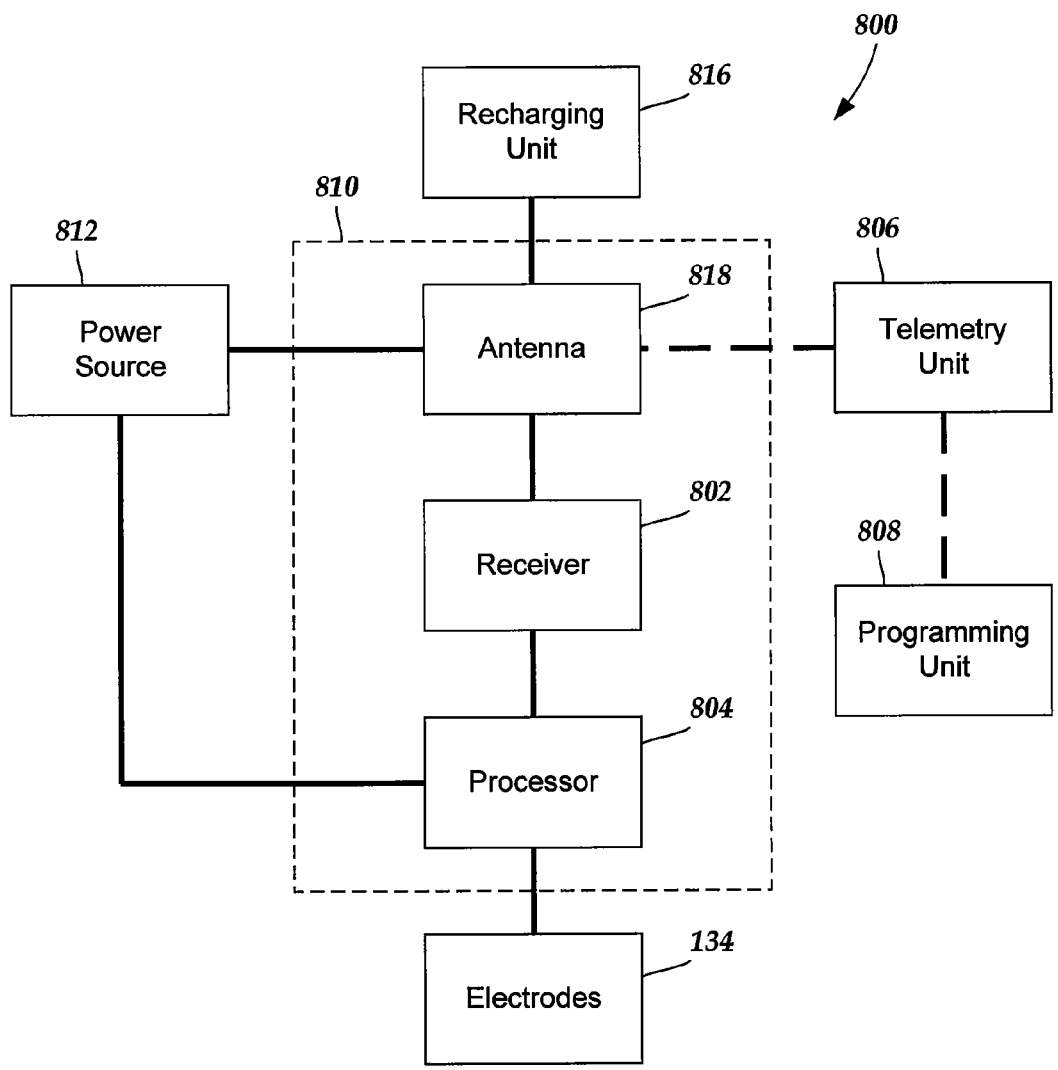
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 1506. The telemetry unit 1506 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

The invention claimed is:

1. A method for forming a lead or lead extension comprising an arrangement of a plurality of elongated conductors disposed in a body of the lead or lead extension, each of the elongated conductors extending from a proximal end of the arrangement to a distal end of the arrangement, the method comprising:

ablating a plurality of spaced-apart transverse channels in at least one of the proximal end or the distal end of the body;

ablating an access hole into each of the plurality of transverse channels defined in the body, each of the access holes individually exposing one of the elongated conductors such that the remaining elongated conductors are not exposed;

disposing C-shaped contacts over each of the access holes such that each C-shaped contact is disposed in a different one of the plurality of transverse channels;

electrically coupling the C-shaped contacts to at least one of the elongated conductors;

closing each of the C-shaped contacts so that the two opposing ends of the C-shaped contacts are adjacent to one another; and for each of the C-shaped contacts, coupling the two opposing ends together such that the C-shaped contact forms a continuous path around the arrangement over the at least one access hole over which the C-shaped contact is disposed.

2. The method of claim 1, wherein the plurality of conductors are disposed in a multi-lumen retention element.

3. The method of claim 2, wherein ablating a plurality of access holes comprises ablating at least a portion of the multi-lumen retention element.

4. The method of claim 1, wherein at least one of the C-shaped contacts is a terminal.

5. The method of claim 1, wherein at least one of the C-shaped contacts is an electrode.

6. The method of claim 1, wherein coupling the two opposing ends of each of the C-shaped contacts together comprises welding the two opposing ends of each of the C-shaped contacts together.

7. The method of claim 1, wherein ablating a plurality of access holes comprises ablating insulation individually disposed over at least one of the conductors.

8. The method of claim 1, wherein ablating a plurality of access holes comprises laser ablating the body of the lead or lead extension.

9. The method of claim 1, wherein electrically coupling the C-shaped contacts to the elongated conductors occurs prior to coupling the opposing ends of the C-shaped contacts together.

10. The method of claim 1, wherein closing each of the C-shaped contacts forms a coupling aperture defined between the opposing inwardly-bending ends of the C-shaped contact.

11. The method of claim 10, further comprising aligning each of the coupling apertures of the closed C-shaped contacts over at least one of the access holes.

12. The method of claim 11, wherein electrically coupling the C-shaped contacts to the elongated conductors occurs, via one of the coupling apertures, while coupling the two opposing ends of each of the C-shaped contacts together.

13. The method of claim 1, wherein ablating a plurality of access holes in at least one of the proximal end or the distal end of the body comprises ablating each of the plurality of access holes such that each of the access holes extends less than a complete circumference around the body.

14. The method of claim 2, wherein each of the plurality of conductors is disposed in a different lumen of the multi-lumen retention element.

15. The method of claim 1, wherein for each of the plurality of transverse channels the transverse channel has a depth that is no greater than a thickness of the C-shaped contact disposed in the transverse channel.

16. The method of claim 15, wherein for at least one of the plurality of transverse channels the transverse channel has a depth that is equal to a thickness of the C-shaped contact disposed in the transverse channel.

17. The method of claim 15, wherein for at least one of the plurality of transverse channels the transverse channel has a depth that is less than a thickness of the C-shaped contact disposed in the transverse channel.

18. The method of claim 15, further comprising for each C-shaped contact disposed in one of the transverse channels having a depth that is less than a thickness of the C-shaped contact grinding down the C-shaped contact such that the C-shaped contact is flush with an outer layer of the lead body.

* * * * *